United States Patent [19]

Ali et al.

[11] 4,179,385

[45] Dec. 18, 1979

[54] PROCESS FOR THE PRODUCTION OF OVERBASED MANGANESE SALTS OF ORGANIC ACIDS

[75] Inventors: Asghar Ali, Edison; Robert Caruso, Westfield, both of N.J.; Alfred Fischer, Forest Hills, N.Y.; Adolph J. Deinet, East Brunswick, N.J.; Pasquale P. Minieri, Woodside, N.Y.; Henri Sidi, Paramus, N.J.

[73] Assignee: Tenneco Chemicals, Inc., Saddle Brook, N.J.

[21] Appl. No.: 902,464

[22] Filed: May 3, 1978

[51] Int. Cl.$^2$ .................... C10M 1/40; C10M 1/24; C10M 3/34; C10L 1/24
[52] U.S. Cl. ........................................ 252/33; 44/51; 252/35
[58] Field of Search .................. 44/51; 252/33, 35

[56] References Cited

U.S. PATENT DOCUMENTS

| | | | |
|---|---|---|---|
| 3,492,230 | 1/1970 | Watson et al. | 252/33 |
| 3,629,109 | 12/1971 | Gergel et al. | 252/33 |
| 3,827,979 | 8/1974 | Piotrowski et al. | 252/33 |
| 3,857,790 | 12/1974 | Saunders et al. | 252/33 |

Primary Examiner—Irving Vaughn
Attorney, Agent, or Firm—Evelyn Berlow

[57] ABSTRACT

Solutions of overbased manganese salts of organic acids that contain from 20% to 28% by weight of manganese are prepared by (a) carbonating a reaction mixture that contains excess manganous oxide, an organic acid, a promoter, a copromoter, a solvent system, and 0.3% to 0.8% by weight of water, based on the weight of the solvent system, at a temperature in the range of 50° C. to 100° C. at a pressure in the range of 1 atmosphere to 10 atmospheres, thereby forming a solution of overbased manganese salt that contains 2% to 10% by weight of manganese, and (b) heating said solution under subatmospheric pressure to separate a distillate from a residue that is a solution of overbased manganese salt that contains 20% to 28% by weight of manganese.

16 Claims, No Drawings

PROCESS FOR THE PRODUCTION OF OVERBASED MANGANESE SALTS OF ORGANIC ACIDS

This invention relates to a process for the production of overbased oil-soluble manganese salts of organic acids. More particularly, it relates to a process for the production of overbased manganese salts by carbonation of a system comprising a manganese compound and an organic acid in the presence of a promoter, a copromoter, solvent and water.

Overbased manganese salts of organic acids, which are compounds in which manganese is present in excess of the stoichiometric amount required to react with the acidic groups of the organic acids, are widely used as additives in liquid hydrocarbon fuels and in lubricants for internal combustion engines. The basicity of these additives counteracts the corrosive acidic compounds that are formed during the operation of the engines and inhibits the formation of deposits of soot, lacquer, and sludge in the engines. In addition, these additives act as smoke suppressants in the fuels and improve the detergency of the lubricants.

The overbased salts are commonly produced by a process in which a basic manganese compound, such as manganous oxide, is suspended in an inert solvent containing an organic acid, a promoter, and a copromoter, and an acidic gas, which is usually carbon dioxide, is passed through the suspension to reduce its basicity. This process produces a product in which the manganese compound is complexed or dispersed in the solvent.

Modifications of this process have been disclosed in a number of patents. For example, in U.S. Pat. No. 3,544,463, Koft disclosed a process in which the preparation of overbased salts of alkaline earth metals was carried out under anhydrous conditions in the presence of a halide, such as zinc chloride, stannous chloride, ammonium chloride, or chloranil. Watson et al. disclosed in U.S. Pat. No. 3,492,230 the use of ethylene diamine and water to promote the carbonation reaction with magnesium oxide, while Sanders et al. in U.S. Pat. No. 3,857,790 carried out the carbonation reaction using a basic magnesium compound in the presence of a hydroxyl-containing compound, an amine salt such as the diformate of ethylene diamine, and 5% to 50%, based on the weight of solvent, of water. Sabol et al. disclosed in U.S. Pat. No. 3,524,814 a process in which the carbonation of alkaline earth metal oxides and organic acids was carried out in the presence of ammonium carbamate. In U.S. Pat. No. 2,695,910, Asseff et al. disclosed a process in which overbased metal salts are prepared by the reaction of an alkaline earth metal compound with an acidic compound, a promoter that is, e.g., a phenolic compound, and preferably 5 to 50 moles of water per mole of the alkaline earth metal compound.

In U.S. Pat. No. 3,827,979, Piotrowski et al. reported that when organic acids are overbased with manganous oxide in a carbonation process both a promoter and a copromoter must be present in the system if a highly-overbased product is to be obtained. While the process disclosed by Piotrowski et al. does yield highly-overbased manganese salts, it takes place too slowly to be useful commercially, and it converts only a portion of the manganous oxide to an oil-soluble overbased manganese salt.

This invention relates to an improved process for the production of overbased manganese salts that quickly and efficiently converts manganous oxide to highly overbased manganese salts of organic acids. This process involves contacting with carbon dioxide at a pressure in the range of 1 atmosphere to 10 atmospheres a dispersion that contains (1) manganous oxide, (2) at least one organic carboxylic acid or organic sulfonic acid, (3) a promoter selected from the group consisting of ammonium halides, ammonium nitrate, mono-, di-, and trialkylamine hydrohalides, ammonium sulfide, and ammonium peroxydisulfate, (4) a copromoter that is a metal halide, (5) water, and (6) a solvent system that comprises an alcohol and an inert hydrocarbon or halogenated hydrocarbon. The products of this carbonation reaction are overbased manganese salt solutions that contain from 2% to 10% by weight of manganese and that can be concentrated to clear, fluid products containing high levels of manganese, usually from 20% to 28% by weight of manganese, that are useful as additives for fuel oils and lubricants.

In addition to providing high yields of overbased manganese salt solutions that contain at least 20% by weight of manganese, the process of this invention has the advantages of yielding these products in reaction times that are far shorter than those required by the processes of the prior art and of consuming much less carbon dioxide than do those processes.

In the process of this invention, a reaction mixture that contains manganous oxide, an organic acid, a solvent system, a promoter, a copromoter, and a small amount of water is contacted with carbon dioxide while it is maintained at a temperature in the range of 50° C. to 100° C. at a pressure in the range of 1 atmosphere to 10 atmospheres until the carbonation is complete and the reaction mixture is a solution of an overbased manganese salt that contains from 2% to 10%, preferably 4% to 6%, by weight of manganese.

The organic acids, promoters, copromoters, and solvent system that are used in the practice of this invention include those that were disclosed by Piotrowski et al. in U.S. Pat. No. 3,827,979, which is incorporated herein by reference.

The organic acids that are used in the process of this invention are organic carboxylic acids and organic sulfonic acids that are oil soluble and that form manganese salts that are oil soluble. They are preferably aliphatic and cycloaliphatic monocarboxylic acids having 4 to 10 carbon atoms, aromatic monocarboxylic acids having 7 to 12 carbon atoms, and mixtures thereof. Examples of these preferred acids include butyric acid, valeric acid, hexanoic acid, heptanoic acid, n-octanoic acid, 2-ethylhexanoic acid, n-nonanoic acid, isononanoic acid, neononanoic acid, n-decanoic acid, neodecanoic acid, naphthenic acids, benzoic acid, toluic acid, tert.-butylbenzoic acid, hydroxybenzoic acids, chlorobenzoic acids, chlorotoluic acids, and the like.

The relative amounts of manganous oxide and the organic acid used are not critical provided that a stoichiometric excess of manganous oxide is present. In most cases a 5% to 100% molar excess of manganous oxide is used.

The promoters that are used in the process of this invention include ammonium halides, ammonium nitrate, mono-, di-, and trialkylamine hydrochlorides, ammonium sulfide and ammonium peroxydisulfate. Among the useful copromoters are alkaline earth metal halides, aluminum chloride, and ferric chloride. The reaction mixture usually contains from 1% to 10% by weight of the promoter and from 1% to 10% by weight of the copromoter, based on the weight of manganous oxide in the reaction mixture. Excellent results have been obtained using 3% to 5% of ammonium chloride as the promoter and 7% to 9% of calcium chloride or barium chloride as the copromoter, based on the weight of manganous oxide in the reaction mixture.

The solvent system in which the carbonation reaction is carried out contains from 10% to 90% by weight of an alcohol that may be a monohydric alcohol having 1 to 12 carbon atoms, a glycol having 2 to 8 carbon atoms, or a mixture of these alcohols and from 10% to 90% by weight of an inert solvent that is a hydrocarbon and/or a halogenated hydrocarbon. The solvent system preferably contains 15% to 40% by weight of a monohydric alcohol, such as methanol, 2-propanol, 2-methoxyethanol, or ethylene glycol and 60% to 85% by weight of a liquid hydrocarbon or halogenated hydrocarbon, such as benzene, toluene, xylene, chlorobenzene, chlorotoluene, dichlorotoluene, naphtha, hexane, petroleum ether, or kerosene. Best results have been obtained using a solvent system that contained 30% to 35% by weight of 2-methoxyethanol and 65% to 70% by weight of naphtha and having a pH in the range of 1.5 to 2.5, as measured on an aqueous extract obtained by contacting a portion of the solvent system with an equal volume of distilled water. The amount of the solvent system that is used is that which will yield a reaction product that is an overbased manganese salt solution that contains 2% to 10% and preferably 4% to 6% by weight of manganese.

The amount of water that is in the reaction mixture is that which will catalyze the carbonation reaction and cause this reaction to take place quickly and to give a nearly quantitative yield of highly overbased manganese salt. As little as 0.3% by weight of water, based on the weight of the solvent system, will increase the rate at which the carbonation reaction takes place. When there is more than 0.8% by weight of water, based on the weight of the solvent system, in the reaction mixture, the yield of overbased manganese salt is generally reduced, probably because in the presence of excess water some of the manganous oxide is converted to insoluble manganese compounds that precipitate from the reaction mixture. Optimum rate of reaction and yield result when the reaction mixture contains at the start of the carbonation reaction from 0.5% to 0.6% by weight of water, based on the weight of the solvent system. During the reaction, the water content of the reaction mixture rises as water is formed as a by-product of the salt-forming reaction. When the amount of the solvent system in the reaction mixture is that which will yield an overbased manganese salt solution that contains from 4% to 6% by weight of manganese, the reaction mixture contains from 0.1 mole to 0.4 mole of water per mole of manganous oxide. During the carbonation reaction, the reaction mixture is maintained at a temperature in the range of 50° to 100° C. and a pressure in the range of 1 atmosphere to 10 atmospheres. It is preferably maintained at a temperature in the range of 90° to 97° C. and a pressure in the range of 1.5 atmospheres to 3.5 atmospheres.

When the carbonation reaction has been completed, the reaction product is an overbased manganese salt solution that contains from 2% to 10% by weight and in most cases from 4% to 6% by weight of manganese. After filtration, the solution is usually heated under subatmospheric pressure to distill off a portion of the solvent system and to increase the manganese content of the solution to at least 20% by weight. In a preferred concentration procedure, the solution that contains 2% to 10% by weight of manganese is heated to about 65° C. at a pressure in the range of 100 mm to 150 mm mercury absolute to separate a first distillate that constitutes 7% to 10% of the weight of the original solution and a first residue. The first residue is then heated to about 75° C. at a pressure in the range of 100 mm to 150 mm mercury absolute to separate a second distillate that constitutes about 10% of the weight of the first residue from the second residue. The first and second distillates may be recovered and recycled, or they may be discarded. The second residue is then heated to about 120° C. at a pressure in the range of 100 mm to 150 mm mercury absolute to separate a third distillate from a third residue that is an overbased manganese salt solution that contains from 20% to 28% by weight of manganese and substantially no water. The third distillate is ordinarily reconstituted by the procedure set forth hereinafter and recycled.

The process of this invention may be carried out as a batch, semi-continuous, or continuous process.

In a preferred embodiment of the invention, the solvent system in which the carbonation reaction is carried out is a reconstituted solvent system that is made up of fresh solvent and solvent that has been recovered from the concentration step of a previous run and treated to bring its water content to the desired level and to remove from it reaction by-products that can inhibit the salt-forming reaction. The recovered solvent may, for example, be acidified with hydrogen chloride, formic acid, acetic acid, sulfuric acid, phosphoric acid, or other acids to pH 1.5–2.5, as measured on an aqueous extract obtained by contacting a portion of the solvent system with an equal volume of distilled water. This acidification, which is best carried out by sparging the recovered solvent mixture with anhydrous hydrogen chloride, neutralizes any ammonia or other alkaline compounds that are present and activates the manganous oxide, thereby shortening the initiation period and accelerating the rate at which the salt-forming reaction takes place. The water content of the acidified recovered solvent mixture is brought to the desired level either by distillation to remove excess water or by the addition of water.

To the recovered solvent mixture that has been treated in this way are added the amounts of alcohol and hydrocarbon or halogenated hydrocarbon that are necessary to replace those removed as distillation forecuts and those that remain in the distillation residue that is the overbased manganese salt solution, thereby forming a reconstituted solvent system that has the same composition as the original solvent system.

The invention is further illustrated by the following examples. In these examples, all parts are parts by weight, and all percentages are percentages by weight.

EXAMPLE 1

A series of manganese salts of monocarboxylic acids was prepared by the following procedure:

Dispersions that contained 0.333 mole (calculated from the acid number) of an organic monocarboxylic acid, 50 grams (0.698 mole) of manganous oxide, 2 grams of ammonium chloride, 4 grams of anhydrous calcium chloride, 500 ml. of naphtha (boiling range, 160°–167° C.) and 225 ml. of 2-methoxyethanol were stirred and heated to 90°–95° C. The dispersions were carbonated at 90°–95° C. Under atmospheric pressure using an excess of carbon dioxide over the amount required for the carbonation reaction for periods ranging from 10 minutes to 5.25 hours. During this time, no carbonation took place, as was indicated by the unchanged appearance of the dispersions.

Then 5 grams of water was added to each of the dispersions, and the treatment with carbon dioxide at 90°–95° C. was continued. The carbonation reaction began within 5 to 30 minutes after the addition of water, as was shown by a change in the color of the reaction mixtures. When the reaction has been completed and the absorption of carbon dioxide had ceased, the reaction products were cooled, treated with filter aid, and filtered.

The monocarboxylic acids and reaction conditions used and the results obtained are shown in Table I.

Each of the reaction products was distilled under vacuum to bring its manganese content to 22%.

Table I

| Ex. No. | Acid Used | Carbonation Time at 90°–95° C. Prior to Addition of Water (Hrs.) | After Addition of Water (Hrs.) | % of Charged Mn in Reaction Product | % Mn Overbasing |
|---|---|---|---|---|---|
| 1A | Valeric | 1 | 4.25 | 95.9 | 301 |
| 1B | Heptanoic | 1 | 4.25 | 94.7 | 296 |
| 1C | n-Octanoic | 1 | 8.75 | 95.3 | 293 |
| 1D | 2-Ethylhexanoic | 1.5 | 7.25 | 97.8 | 308 |
| 1E | Isononanoic | 0.16 | 9 | 91.4 | 283 |
| 1F | Naphthenic | 5.25 | 5.5 | 95.3 | 298 |
| 1G | Benzoic | 1 | 3.75 | 100 | 320 |

EXAMPLE 2

To a one-liter flask equipped with a heating mantle, thermometer, gas inlet tube, stirrer, and reflux condenser were charged 43.5 grams (0.333 mole) of heptanoic acid, 50 grams (0.698 mole) of manganous oxide (99% MnO), 2 grams of ammonium chloride, 4 grams of anhydrous calcium chloride, 431 grams of naphtha (boiling range, 160°–167° C.), and 215 grams of 2-methoxyethanol. The reaction mixture was stirred at 90°–95° C. under atmospheric pressure and sparged with carbon dioxide for one hour. Then 5 grams of water was added, and the reaction mixture at 90°–95° C. was sparged with carbon dioxide at the range of 90 ml./minute for 5 hours. After the addition of 2 grams of filter aid, the reaction product was cooled to 25° C. and filtered. The filter cake was washed with 70 grams of naphtha, and the washings were combined with the filtrate to give 685 grams of an overbased manganese heptanoate solution that contained 4.5% of manganese. The yield of overbased manganese heptanoate was 80.4%, based on the weight of manganous oxide charged.

EXAMPLE 3

The procedure described in Example 2 was repeated, except that the carbon dioxide flow rate was 170 ml./minute. A yield of 91.6%, based on the weight of manganous oxide charged, of overbased manganese heptanoate was obtained.

EXAMPLE 4

To a one-liter, stainless steel autoclave were charged 43.5 grams (0.333 mole) of heptanoic acid, 50 grams (0.698 mole) of manganous oxide (99% MnO), 2 grams of ammonium chloride, 4 grams of anhydrous calcium chloride, 431 grams of naphtha (boiling range, 160°–167° C.); and 215 ml. of 2-methoxyethanol.

The autoclave was sealed and sparged with carbon dioxide to remove air from it. The reaction mixture was then stirred and heated at 90°–95° C. for one hour during which time the pressure in the autoclave was maintained at 2 atmospheres by the addition of carbon dioxide as needed. Then 5 grams of water was added, and the reaction mixture was stirred at 90°–95° C. under a pressure of 2 atmospheres for five hours.

Two grams of filter aid was added to the reaction product, which was then cooled to 25° C. and filtered. The filter cake was washed with 70 grams of naphtha, and the washings were combined with the filtrate. The resulting overbased manganese heptanoate solution, which contained 5.0% of manganese, was obtained in a yield of 99.4%, based on the weight of manganous oxide charged.

EXAMPLE 5

When the procedure described in Example 4 was repeated except that the reaction mixture was heated for 2.5 hours after the addition of water, a 97.5% yield of overbased manganese heptanoate, based on the weight of manganous oxide charged, was obtained.

The product was distilled under vacuum until it contained 24% of manganese.

EXAMPLE 6

A. To a mixture that contained 173.5 parts of 2-methoxyethanol and 346.5 parts of naphtha (boiling range, 160°–175° C.) was added 1.7 parts of water. The resulting solvent mixture, which had a moisture content of 0.5%, was acidified with anhydrous hydrogen chloride to pH 1.5–2.0 and then sparged with nitrogen to remove residual hydrogen chloride from it. The resulting solvent mixture, which had a pH of 1.8, was stirred at room temperature while 35 parts of heptanoic acid, 40.5 parts of manganous oxide, 1.5 parts of ammonium chloride, and 3.2 parts of anhydrous calcium chloride were added to it.

B. The vessel that contained the reaction mixture was evacuated to a vacuum of 25 inches mercury, pressurized with carbon dioxide to 15 psig, re-evacuated to a vacuum of 25 inches mercury, and again pressurized to 15 psig with carbon dioxide.

The reation mixture was then stirred and heated at 91°–96° C. while the pressure was maintained at 15 psig by the addition of carbon dioxide. After the reaction mixture had been heated under these conditions for 2 hours, the carbonation reaction began, as was shown by a sharp exotherm and by the rapid absorption of carbon dioxide. During the 3 hour reaction period, external cooling was necessary to maintain the temperature between 91° and 96° C., and a total of 22.5 parts carbon dioxide was added when necessary to maintain the pressure at 15 psig.

The reaction product was cooled to 65° C., treated with filter-aid, and filtered. There was obtained 594 parts of a crude overbased manganese salt solution that contained about 5% manganese.

C. After the addition of 0.6 part of an anti-foaming agent (SAG-47) and 437 parts of naphtha (boiling range, 160° C.–175° C.) to it, the crude product was distilled under a pressure of 120 mm mercury absolute to 112° C. to separate 443.5 parts of distillate from the manganese salt solution. There was obtained 135 parts of an overbased manganese heptanoate solution that contained 22% manganese and that had a Gardner-Holdt viscosity at 25° C. of A-4. The yield, based on manganous oxide charged, was 94.8%.

EXAMPLE 7

A. The solvent that was separated as the distillate when the crude product formed in Step B was distilled in Step C of Example 6 contained 31% of 2-methoxyethanol, 68.4% of naphtha, and 0.6% of water. It was acidified to pH 2.4 with anhydrous hydrogen chloride and then combined with 41 parts of 2-methoxyethanol and 54.5 parts of naphtha to form a reconstituted solvent mixture that contained 0.54% of water and had a pH of 2.0.

To the reconstituted solvent mixture were added 35 parts of heptanoic acid, 40.5 parts of manganous oxide, 1.5 parts of ammonium chloride, and 3.2 parts of anhydrous calcium chloride. This reaction mixture was heated with carbon dioxide at 90°–95° C. under the pressure of 15 psig. After the mixture had been stirred for 1.75 hours at this temperature and pressure, the carbonation reaction began. It was continued under these conditions for 3 hours, when there was no further absorption of carbon dioxide. The reaction product was cooled and filtered to yield a crude product that contained 5.3% manganese. A quantitative yield of the overbased manganese salt was obtained.

B. The crude product was distilled under a pressure of 120 mm mercury absolute to 120° C. to separate a distillate from the residue that contained 22% manganese and had a Gardner-Holdt viscosity at 25° C. of A-2.

EXAMPLE 8

A. The distillate that was separated in Step B of Example 7 was a mixture of 2-methoxyethanol and naphtha that contained 0.65% of water. This distillate was acidified to pH 2.2 with anhydrous hydrogen chloride and then reconstituted and used in the preparation of an overbased manganese salt by the procedures described in Example 7A. The carbonation reaction began after the reaction mixture had been heated at 90°–95° C. under a pressure of 15 psig for 0.9 hour. There was obtained a 95% yield of the overbased manganese salt as a solution that contained 5% of manganese.

B. The solution of overbased manganese heptanoate was distilled under a pressure of 120 mm mercury absolute until it had a manganese content of 22%. This solution had a Gardner-Holdt viscosity at 25° C. of J.

EXAMPLE 9

The distillate that was separated from the product in Example 8B was a mixture of 2-methoxyethanol and naphtha that contained 0.4% of water. This distillate was acidified to pH 1.8 with anhydrous hydrogen chloride and after reconstitution was used as the solvent mixture in the preparation of overbased manganese heptanoate by the procedure described in Example 7A. The carbonation reaction began as soon as the reaction mixture reached 90° C. There was obtained an 88% yield of overbased manganese heptanoate as a solution that contained 4.6% Mn.

What is claimed is:

1. In the process for the production of overbased manganese salts of organic acids that comprises contacting with carbon dioxide at a temperature in the range of 50° C. to 100° C. until the carbonation reaction is complete a reaction mixture that comprises (1) excess manganous oxide, (2) an organic acid selected from the group consisting of oil-soluble organic carboxylic acids and oil-soluble organic sulfonic acids, (3) a promoter selected from the group consisting of ammonium halides, ammonium nitrate, mono, di-, and trihydrocarbyl amine hydrohalides containing 1 to 3 carbon atoms, ammonium sulfide, and ammonium peroxysulfate, (4) a copromoter selected from the group consisting of alkaline earth halides, aluminum chloride, and ferric chloride, and (5) a solvent system containing from 10% to 90% by weight of an alcohol having from 1 to 18 carbon atoms and from 10% to 90% by weight of an inert solvent selected from the group consisting of hydrocarbons, halogenated hydrocarbons, and mixtures thereof, wherein the proportion of promoter and copromoter is from 2% to 20%, based on the weight of manganous oxide, and the amount of the solvent system is that which will produce a product that contains from 2% to 10% by weight of manganese, the improvement that comprises carrying out the carbonation reaction at a pressure in the range of 1 atmosphere to 10 atmospheres in the presence of from 0.3% to 0.8% of water, based on the weight of the solvent system in the reaction mixture.

2. The process of claim 1 wherein the solvent system has a pH in the range of 1.5 to 2.5, as measured on an aqueous extract obtained by contacting a portion of the solvent system with an equal volume of distilled water.

3. The process of claim 1 wherein the reaction mixture is maintained at a temperature in the range of 90° C. to 97° C. and at a pressure in the range of 1.5 atmospheres to 3.5 atmospheres during the carbonation reaction.

4. The process of claim 1 wherein the reaction mixture contains 0.5% to 0.6% by weight, based on the weight of the solvent system, of water during the carbonation reaction.

5. The process of claim 1 wherein the reaction mixture comprises excess manganous oxide, heptanoic acid, ammonium chloride, calcium chloride, water, naphtha, and 2-methoxyethanol.

6. The process of claim 1 wherein the solvent system contains 15% to 40% by weight of a monohydric alcohol and 60% to 85% by weight of a liquid hydrocarbon.

7. The process of claim 1 wherein the solvent system contains 30% to 35% by weight of 2-methoxyethanol and 65% to 70% by weight of naphtha.

8. The process of claim 1 wherein the amount of the solvent system used is that which will produce a product that contains from 4% to 6% by weight of manganese.

9. The process of claim 1 wherein the solution of overbased manganese salt that contains from 2% to 10% by weight of manganese is distilled to separate a solvent fraction from a residue that contains from 20% to 28% by weight of manganese.

10. The process for the production of overbased manganese salts of organic acids that comprises the steps of
(a) forming a solvent system that contains from 10% to 90% by weight of an alcohol having from 1 to 18 carbon atoms, from 10% to 90% by weight of an inert solvent selected from the group consisting of hydrocarbons, halogenated hydrocarbons, and mixtures thereof, and 0.3% to 0.8% by weight of water and that has a pH in the range of 1.5 to 2.5, as measured on an aqueous extract obtained by contacting a portion of the solvent system with an equal volume of distilled water;
(b) forming a reaction mixture by adding to the solvent system (1) excess manganous oxide, (2) an organic acid selected from the group consisting of oil-soluble organic carboxylic acids and oil-soluble organic sulfonic acids, (3) a promoter selected from the group consisting of ammonium halides, ammonium nitrate, mono-, di-, and trihydrocarbyl amine hydrohalides containing 1 to 3 carbon atoms, ammonium sulfide, and ammonium peroxysulfate, and (4) a copromoter selected from the group consisting of alkaline earth halides, aluminum chloride, and ferric chloride, in the amounts of 2% to 20%, based on the weight of manganous oxide, of the promoter and copromoter and amounts of manganous oxide and organic acid that will produce a product that contains from 2% to 10% by weight of manganese;
(c) maintaining said reaction mixture at a temperature in the range of 50° C. to 100° C. and at a pressure in the range of 1 atmosphere to 10 atmospheres while contacting it with carbon dioxide to reduce its basicity, thereby forming a solution of overbased manganese salt that contains from 2% to 10% by weight of manganese;
(d) heating said solution of overbased manganese salt under subatmospheric pressure to separate a distillate that comprises alcohol and inert solvent from a residue that is a solution of overbased manganese salt that contains from 20% to 28% by weight of manganese;
(e) adding to said distillate the amounts of alcohol and inert solvent needed to restore the solvent system to its original composition, thereby forming a reconstituted solvent system;
(f) adjusting the water content of the reconstituted solvent system to 0.3% to 0.8% by weight;
(g) acidifying the reconstituted solvent system to pH 1.5–2.5;
(h) recycling the resulting acidified reconstituted solvent system to Step (b); and
(i) repeating Steps (b) to (h).

11. The process of claim 10 wherein the solvent system formed in Step (a) contains 0.5% to 0.6% by weight of water.

12. The process of claim 10 wherein the solvent system formed in Step (a) contains 15% to 40% by weight of a monohydric alcohol, 60% to 85% by weight of a liquid hydrocarbon, and 0.5% to 0.6% by weight of water.

13. The process of claim 10 wherein the reaction mixture formed in Step (b) contains an amount of the solvent system that will produce a product that contains 4% to 6% by weight of manganese.

14. The process of claim 10 wherein in Step (c) the reaction mixture is maintained at a temperature in the range of 90° C. to 97° C. and at a pressure in the range of 1.5 atmospheres to 3.5 atmospheres during the carbonation reaction.

15. The process of claim 10 wherein in Step (d) the solution of overbased manganese salt that contains 2% to 10% by weight of manganese is heated to about 120° C. at a pressure in the range of 100 mm to 150 mm mercury absolute to separate a distillate from a residue that is a solution of overbased manganese salt that contains 20% to 28% by weight of manganese.

16. The process of claim 10 wherein in Step (d) the solution of overbased manganese salt that contains 2% to 10% by weight of manganese is heated to about 65° C. at a pressure in the range of 100 mm to 150 mm mercury absolute to separate a first distillate, which constitutes 7% to 10% of the weight of said solution and which is discarded, from a first residue; the first residue is heated to about 75° C. at a pressure in the range of 100 mm to 150 mm mercury absolute to separate a second distillate that constitutes about 10% of the weight of the first residue from a second residue; and the second residue is heated to about 120° C. at a pressure in the range of 100 mm to 150 mm mercury absolute to separate a third distillate from a third residue that is an overbased manganese salt solution that contains from 20% to 28% by weight of manganese.

* * * * *